United States Patent [19]
Norfleet et al.

[11] Patent Number: 5,505,933
[45] Date of Patent: Apr. 9, 1996

[54] DESENSITIZING ANTI-TARTAR DENTIFRICE

[75] Inventors: James Norfleet, Plainfield; Willie J. Carter, Belle Mead; Matthew J. Frankel, Franklin Park; Abdul Gaffar, Princeton, all of N.J.

[73] Assignee: Colgate Palmolive Company, New York, N.Y.

[21] Appl. No.: 405,047

[22] Filed: Mar. 15, 1995

Related U.S. Application Data

[62] Division of Ser. No. 265,883, Jun. 27, 1994.

[51] Int. Cl.$^6$ .......................... A61K 7/16; A61K 7/18
[52] U.S. Cl. .......................... 424/52; 424/49; 424/57
[58] Field of Search .......................... 424/49–58

[56] References Cited

U.S. PATENT DOCUMENTS

| | | | |
|---|---|---|---|
| 3,821,117 | 6/1974 | Breece et al. | 252/99 |
| 3,863,006 | 1/1975 | Hodosh | 424/49 |
| 4,057,621 | 11/1977 | Pashley et al. | 424/49 |
| 4,283,385 | 8/1981 | Dhabhar et al. | 424/52 |
| 4,357,318 | 11/1982 | Shah et al. | 424/52 |
| 4,631,185 | 12/1986 | Kim | 424/49 |
| 4,645,662 | 2/1987 | Nakashima et al. | 424/52 |
| 4,701,223 | 10/1987 | Eoga | 134/2 |
| 4,751,072 | 6/1988 | Kim | 424/49 |
| 4,806,340 | 2/1989 | Gaffar et al. | 424/52 |
| 4,807,649 | 2/1989 | Eoga | 134/2 |
| 4,889,712 | 12/1989 | Gaffar et al. | 424/52 |
| 4,894,220 | 1/1990 | Nabi et al. | 424/52 |
| 4,925,654 | 5/1990 | Gaffar et al. | 424/52 |
| 4,931,273 | 6/1990 | Gaffar et al. | 424/52 |
| 4,933,171 | 6/1990 | Bristow et al. | 424/47 |
| 4,992,258 | 2/1991 | Mason | 424/49 |
| 5,015,466 | 5/1991 | Parran et al. | 424/52 |
| 5,015,467 | 5/1991 | Smither et al. | 424/52 |
| 5,037,635 | 8/1991 | Nabi et al. | 424/52 |
| 5,087,444 | 2/1992 | Jackson et al. | 424/52 |
| 5,156,835 | 10/1992 | Nabi et al. | 424/52 |
| 5,180,578 | 1/1993 | Gaffar et al. | 424/52 |
| 5,188,820 | 2/1993 | Cummins et al. | 424/52 |
| 5,234,688 | 8/1993 | Gaffar et al. | 424/52 |
| 5,240,697 | 8/1993 | Norfleet et al. | 424/52 |
| 5,252,577 | 10/1993 | Brever et al. | 424/49 |
| 5,256,402 | 10/1993 | Prencipe et al. | 424/53 |
| 5,260,062 | 11/1993 | Gaffar et al. | 424/52 |
| 5,268,167 | 12/1993 | Tung | 424/52 |
| 5,270,031 | 12/1993 | Lim et al. | 424/49 |
| 5,292,526 | 3/1994 | Gaffar et al. | 424/52 |
| 5,334,375 | 8/1994 | Nabi et al. | 424/52 |
| 5,352,439 | 10/1994 | Norfleet et al. | 424/52 |
| 5,374,417 | 12/1994 | Norfleet et al. | 424/52 |

FOREIGN PATENT DOCUMENTS 9200721  1/1992  WIPO.

OTHER PUBLICATIONS

Derwent Abstract of WO/PCT 9200721 (Jan. 23, 1990) Nelson & Smitherman (16 p.) (U.S. Jul. 11, 1992).
Derwent Abstract of Lion JP 59167509 (Sep. 21, 1984) (Potassium Hydroxide & Potassium Dinhosphon).

*Primary Examiner*—Shep K. Rose
*Attorney, Agent, or Firm*—Murray M. Grill; Robert L. Stone

[57] ABSTRACT

An oral composition, such as a toothpaste, includes an anti-tartar proportion of a polyphosphate anti-tartar agent (preferably with synthetic anionic polymeric polycarboxylate or equivalent, and fluoride) and a desensitizing proportion of a tooth pain inhibiting potassium salt which passes through exposed dentin tubules to tooth nerves or neurons, which salt can be potassium nitrate, potassium citrate or potassium oxalate, so that it helps to prevent tartar from forming on the teeth and also lessens any pain experienced by persons contacting their sensitive teeth with the oral composition. Preferably the oral composition is a desensitizing anti-tartar toothpaste or gel which, when the teeth are brushed with it, aids in removal of at least some tartar and prevents its reappearance, and at the same time diminishes any tooth pain that the brusher would otherwise experience due to such brushing. In preferred toothpastes the anti-tartar agent and the desensitizing agent are both potassium compounds and other components of the toothpaste, such as the detergent or surfactant, thickener, water soluble fluoride, anionic polymeric polycarboxylate, sweetener and any anti-calculus agent present, when they may be present as salts, will also be potassium salts. In place of the mentioned anti-tartar agents there may be employed other anti-calculus compounds, such as AHP (azacycloheptane-2-2-diphosphonic acid) or corresponding alkali metal salt, preferably the potassium salt, and in such case it is very desirable for other components of the toothpaste to be in the forms of their potassium salts.

15 Claims, No Drawings

DESENSITIZING ANTI-TARTAR DENTIFRICE

This is a division of application Ser. No. 08/265,883 filed on Jun. 27, 1994.

This invention relates to desensitizing anti-tartar dentifrices and to a process for manufacturing them. More particularly, it relates to such a dentifrice which includes a polyphosphate anti-tartar agent, such as tetrapotassium pyrophosphate, with a desensitizing agent which is a tooth pain inhibiting potassium salt, which is capable of passing through exposed dentin tubules to tooth nerves or neurons. Such salts include potassium nitrate, potassium citrate, potassium oxalate and mixtures thereof.

Prior to the present invention it was known to utilize polyphosphates, such as pyrophosphates, as anti-tartar agents in oral compositions, including toothpastes and gels. In U.S. Pat. No. 4,931,273 there are disclosed toothpastes containing tetrapotassium pyrophosphate as an anti-calculus (anti-tartar) agent. This patent and others teach that fluoride has been used in hardening the teeth and that polymeric polycarboxylates have been used as anti-calculus agents. The patent also teaches that both fluoride and polymeric polycarboxylates help to prevent hydrolysis and enzymatic degradation of pyrophosphate.

U.S. Pat. No. 3,863,006 discloses that nitrates, such as potassium nitrate, when incorporated in aqueous solutions or in toothpastes, desensitize the teeth during toothbrushing. Thus toothpastes that contain potassium nitrate desensitize the teeth and make them less painful or painless during brushing and flossing operations.

"Clinical Preventive Dentistry", Mason et al, Vol., 12, No. 6, January 1991, pages 6–12, titled "Evaluation of Tartar Control Dentifrices in In Vitro Models of Dentin Sensitivity" describes dentin sensitivity reduction with tartar control dentifrices containing PVM/MA copolymer (Gantrez S-97, GAF Corp.) as compamercial desensitizing dentifrices.

U.S. Pat. No. 4,992,258 to Mason describes a desensitizing dentifrice composition containing montmorillinite clay and, optionally, polycarboxylate copolymer such as Gantrez S-97 from GAF Corp.

Although both potassium pyrophosphate and potassium nitrate have been suggested as components of dentifrices, applicants' dentifrice and oral compositions, which contain both in one preparation, are believed to be novel, and their coaction to improve desensitization of the teeth and better tartar control and inhibition is not suggested in any reference or combination of references of which applicants are aware.

In accordance with the present invention, a desensitizing, anti-tartar oral composition comprises an orally acceptable vehicle or base for such composition, an effective anti-tartar proportion of poly phosphate, and a desensitizing or tooth pain inhibiting proportion of a tooth pain inhibiting potassium salt which passes through exposed dentin tubules to tooth nerves and neurons. Among such tooth pain inhibiting compounds there may be mentioned various potassium salts, such as potassium nitrate, potassium citrate, potassium oxalate and mixtures thereof. Preferably, the polyphosphate is potassium pyrophos phate and the composition includes a potassium salt of a copolymer of maleic anhydride or maleic acid with vinyl methyl ether (SAPP, for synthetic anionic polymeric polycarboxylate), potassium fluoride and potassium salt components, such as potassium lauryl sulfate and potassium saccharin. However, providing that the total proportion of potas sium in the composition is sufficient, in combination with the pain inhibiting compound, to improve pain inhibition, the sodium analogues of at least some of such compounds, such as tetrasodium pyrophosphate and disodium pyrophosphate, may be present, at least in part. Also, anti-calculus phosphono compounds may be included in the invented oral compositions, including diphosphonic acids and phosphonoalkane carboxylic acid or their alkali metal salts, such as AHP (azacycloheptane-2,2-diphosphonic acid), PPTA (phosphonopropane tricarboxylic acid), PBTA (phosphonobutane-1, 2, 4-tricarboxylic acid and EHDP (ethanehydroxy diphosphonic acid), each as acid or alkali metal salt, all preferably as potassium salts. It is applicants' theory that the presence of potassium ion in the present compositions aids in desensitizing the teeth in toothpastes and other oral compositions so that the teeth feel less pain than when brushed with control toothpastes that contain non-potassium polyphosphate with potassium nitrate or potassium citrate, and in which other components are non-potassium compounds. In addition to the desensitizing effects of the invented compositions other beneficial results are obtained, due to the coaction of the components. Because tartar is removed and its recurrence is controlled, painful effects from its presence are diminished or eliminated and the pain-inhibiting potassium ions and any pain-inhibiting anions can better pass through any exposed dentin tubules to tooth nerves or neurons, which are thereby desensitized. It is recognized that removing tartar from the teeth may facilitate contact with underlying enamel or dentin of any pain provoking material, such as sugars, but it is considered that the desirable removal of tartar and the fact that it is an object to diminish pain experienced during toothbrushing (at which time the concentrations of desensitizing materials in the mouth and on the teeth are greatest and desensitization is therefore most effective) warrant employment of the invented compositions. Also, the invented compositions, when they contain a synthetic anionic polymeric polycarboxylate (SAPP), such as potassium salt of a copolymer of maleic anhydride or maleic acid with vinyl methyl ether, appear to act to close off or narrow tubules in the dentin that could otherwise allow subsequent penetration to the pump and neurons of pain causing materials, such as sugar solutions. That blockage of such tubules does not prevent passage of pain inhibiting ions to the neurons during toothbrushing because such ions are carried into the tubules with the copolymer and other components and also because they are smaller than sugar molecules and therefore can more easily pass through any restricted passageways or lattices. Another advantage of the invented compositions is that they reduce gum recession, which may in part be due to reduction in tartar deposition at the gum line and the absence of the irritation that it causes.

The principal components of the invented compositions are the polyphosphate and the desensitizing potassium compound, which is a salt. The desensitizing potassium salts utilizable in this invention include potassium nitrate, potassium citrate and potassium oxalate, with the first two being preferred. Mixtures including at least one of such salts are also useful, and in some circumstances they may also be mixed with other water soluble potassium salt(s), which are also capable of releasing potassium ions into the toothpaste and into the mouth and onto the teeth. However, care should be taken in choosing such other potassium salts to ensure that they do not cause the composition to taste objectionably salty or have any other undesirable flavor. It has been found that potassium nitrate and potassium citrate, in the proportions employed in the invented compositions, do not taste objectionably salty or otherwise interfere with the desired taste of the composition, especially when a mint/menthol flavor is employed therein.

The polyphosphates that are components of the invented compositions may be any of various water soluble polyphosphates, including alkali metal pyrophosphates, such as tetrapotassium pyrophosphate, dipotassium pyrophosphate, tetrasodium pyrophosphate and disodium pyrophosphate, with the potassium salts being highly preferred. Instead of the pyrophosphates the tripolyphosphates and other polyphosphates, such as the hexametaphosphates, may be substituted, at least in part, but the potassium pyrophosphates are considered to be superior as anti-tartar agents that help to desensitize the teeth. A most preferred pyrophosphate is tetrapotassium pyrophosphate, but the corresponding tri-, di- and mono-potassium pyrophosphates may also be used, at least in part. The polyphosphates act in these claimed compositions to inhibit tartar development on the teeth that are brushed or otherwise treated with the invented compositions. In conjunction with the desensitizing agents mentioned they improve the desensitizing effects thereof and help to make brushing or other treatment of the teeth painless, while at the same time counteracting the development of tartar on the teeth surfaces and near the gums, which can lead to gum irritation and disease.

Another desirable component of the present compositions, and especially of the toothpastes (or dental creams, gels or dentifrices, as they are also called), is a synthetic anionic polymeric polycarboxylate (SAPP), which acts as a stabilizer for the polyphosphate anti-tartar agent and apparently helps to block access of painful or pain-causing materials, such as sugars, to the tooth nerves. The SAPP's employed in the invented compositions include free acidic forms thereof, as well as water soluble salts of such acids, and very preferably such compounds will be in salt form and the salt will be a potassium salt, which acts to improve desensitizing effects of the oral compositions of the invention. Such salts may be starting materials or the acidic forms may be partially or fully neutralized, as by KOH, during the process of manufacturing the toothpaste. Full neutralization is highly preferred, and is often effected during the making of the toothpaste.

The SAPP-type products are preferably polycarboxylates, typically of M.W's. in the 3,000 to 2,000,000 range, preferably 30,000 or 50,000 to 1,100,000 or 1,500,000 and more preferably about 50,000 to 1,100,000, and most preferably 50,000 to 100,000, as determined by vapor pressure osmometry. Such SAPP's are preferably 1:4 to 4:1 copolymers of maleic anhydride and/or maleic acid with another polymerizable ethlenically unsaturated monomer, which is very preferably methyl vinyl ether. By a different method for measuring molecular weights of polymers, gel permeation chromatography against a polyethylene glycol standard, the molecular weights of preferred SAPP's may be found to be in the range of 500,000 to 1,500,000, more preferably 1,000,000 to 1,100,000, e.g., about 1,090,000. Useful such SAPP's include Gantrezes S-97, AN-119, AN-139 and AN-169, all manufactured by GAF Corporation, which have been reported by the manufacturer to have molecular weights of 70,000, 250,000, 500,000 and 750,000, respectively. Equivalent SAPP's to the Gantrezes are sold by BASF, A.G. in Europe under the Luviform® trademark. However, by gel permeation chromatography Gantrez S-97 is determined to be of a molecular weight in the range of 1,000,000 to 1,100,000. The lower molecular weight that had been determined, 70,000, had been measured by vapor pressure osmometry. The mentioned Gantrezes are all linear copolymers but crosslinked polymers, such as Carbopols® 934, 940 and 941 may be substituted for them, at least in part (1% or more). Descriptions of such polymeric materials and of other dentifrice components are contained in U.S. Pat. Nos. 4,627,977 and 4,931,273, and in U.S. patent application Ser. No. 07/631,232 and British Patent Specification 2235133, the disclosures of which are incorporated herein by reference, as are disclosures of all other patents, applications and publications mentioned in this specification.

Instead of the mentioned polymeric polycarboxylates other SAPP types can be substituted, at least preferably only in part, such as polysulfonates, polysulfonates and polyphosphonates, for instance, typically usually to half the SAPP content. The various polymers of such types may be made by reacting an ethylenically unsaturated organic acid, such as maleic, crotonic, sorbic, alpha-chlorosorbic, cinnamic, muconic, itaconic, citraconic, mesaconic, glutaconic, aconitic, angelic, unbellic or fumaric, acid(s) or anhydride(s), with an appropriate polymerized ethylenically unsaturated carboxylic, sulfonic, sulfuric or phosphonic acid that contains an activated carbon-to-carbon olefinic double bond and at least one carboxylic, sulfonic, sulfuric or phosphonic group. Other olefinic monomers that are copolymerizable with the described acids or anhydrides include vinyl acetate, vinyl chloride, dimethyl maleate, and similar unsaturated monomers, and the copolymers made will contain a sufficient proportion of acidic groups or neutralized or neutralizable acidic groups to make them water soluble or swellable. Some such polycarboxylate copolymers are those disclosed in U.S. Pat. Nos. 4,138,477 and 4,183,914, and include copolymers of maleic anhydride with styrene, isobutylene or vinyl ethyl ether, polyacrylic, polyitaconic and polymaleic acids, and sulfoacrylic oligomers of comparatively low molecular weights, such as Uniroyal® ND-2.

Although Gantrez is preferred, also useful in the present compositions as SAPP's or as substitutes for them in part are carboxyvinyl polymers, such as those described in U.S. Pat. Nos. 3,711,604, 3,911,904, 3,919,409, 3,935,306 and 3,980,767, wherein they were employed as components of toothpastes. Such materials are the Carbopols, mentioned previously, which are polymers of polyacrylic acid crosslinked with minor proportions of polyallyl sucrose or polyallyl pentaerythritol, as crosslinking agents. Instead of such polymers there may be employed polycarbophil, which is polyacrylic acid crosslinked with divinyl glycol.

The water soluble fluoride or source of fluoride ions for the present compositions, which helps to stabilize the pyrophosphate against enzymatic attack, while also contributing its tooth hardening and anti-caries properties to the compositions, may be slightly soluble in water, highly soluble or fully soluble, so long as it can provide such ions in the oral compositions and/or in use, in the mouth. The source of fluoride ions is usually inorganic and a salt and is characterized by an ability to release fluoride ions in water and by relative inertness toward other components of the oral compositions. Among the useful sources of fluoride ions are water soluble alkali metal fluorides, such as sodium and potassium fluorides, copper fluorides, such as cuprous fluoride, tin fluorides, such as stannous fluoride, ammonium fluorosilicate, sodium and ammonium fluorozirconates, sodium and potassium monofluorophosphates, aluminum fluorophosphates (mono-, di- and tri-), and fluorinated sodium calcium pyrophosphate. However, in the present invention it is preferred to employ potassium fluoride, potassium monofluorophosphate or other potassium salt or a mixture thereof because added potassium ion serves to deaden pain stimuli to the tooth nerves, and the salt also is a source of fluoride ion.

The orally acceptable vehicle or base for the invented compositions, when such compositions are toothpastes, as is preferred, will normally include water, humectant, bodying agent, surfactant or detergent, and polishing agent. The water employed may be any potable water but it is preferred that it should be of less than 200 p.p.m. of hardness, as $CaCo_3$, and more preferably less than 100 p.p.m. of hardness. Most preferably deionized and irradiated water will be employed. The water and humectant comprise the liquid portion of the toothpaste. The humectant component of the toothpaste will preferably comprise a mixture of several humectants, such as glycerol, sorbitol and polyethylene glycol, which is most preferred, but other mixtures of humectants and single humectants may also be employed. Among other humectants that are useful are propylene glycol and polypropylene glycols. A normal range of molecular weights for the polyethylene glycol humectants is 200 to 1,000, preferably 400 to 600 or 800, e.g., about 600.

The bodying agent, gelling agent or thickener of the toothpaste base may be any such agent but most of these are in the classes of natural and synthetic gums and colloids. Among these may be mentioned carrageenan (Irish moss), xanthan gum and sodium carboxymethyl cellulose, which are preferred, and also gum tragacanth, starch, polyvinylpyrrolidone, hydroxyethylpropylcellulose, hydroxybutyl methyl cellulose, hydroxypropyl methyl cellulose and hydroxyethyl cellulose (which is available as Natrosol®). Inorganic thickeners, such as colloidal silica, e.g., Syloid®244, and synthetic hectorite, such as Laponite®, marketed by Laporte Industries, Ltd., may also be used, and mixtures of such thickeners are also useful.

The surface active agents or surfactant will normally be a water soluble detergent, which is useful to clean the teeth (and gums) and helps the anti-tartar and desensitizing components of the composition to contact the tooth surfaces and to penetrate into the dentin and pulp, where exposed. Such detergents have useful foaming properties and also aid in producing a uniform toothpaste, in which the active components are evenly distributed, so that each toothbrushful of toothpaste will contain effective proportions of such materials. The organic surface-active material is preferably anionic, nonionic or ampholytic in nature, and most preferably is anionic. Suitable examples of anionic surfactants are higher alkyl sulfates such as potassium lauryl sulfate, higher fatty acid monoglyceride monosulfates, such as the potassium salt of the monosulfated monoglyceride of hydrogenated coconut oil fatty acids, alkyl aryl sulfonates such as potassium dodecyl benzene sulfonate, higher fatty sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the potassium salts of N-lauroyl, N-myristoyl, or N-palmitoyl sarcosine which should be substantially free from soap or similar higher fatty acid material. While it is preferred to utilize potassium detergent salts, often such are not commercially available, in which cases sodium salts may be employed (and sometimes such may even be preferred in the described toothpastes).

Examples of water soluble nonionic surfactants are condensation products of ethylene oxide with various hydrogen-containing compounds that are reactive therewith and have lo hydrophobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides (e.g., Pluronic® materials). Of the mentioned detergents the higher fatty alcohol sulfates are preferred (in such detergents and in the other detergents mentioned, and elsewhere in this specification "higher", when employed in designating alkyl groups, fatty acids, etc., identifies such as containing 10 to 20 carbon atoms, preferably 12 to 18, which preferably are in linear arrangement).

The polishing agents of the toothpaste bases are water insoluble materials which are sometimes referred to as abrasives, but they are not intended to remove tooth material but only to remove deposits from and to polish the teeth. Preferred polishing agents are siliceous materials, such as silica, and will normally be of fine particles, such as those of a mean particle size up to about 10 microns and of a very high surface:volume ratio, which may be as much as 250 square meters/gram. A preferred silica is a precipitated amorphous hydrated silica, such as Zeodent® 113 or 115, marketed by J. M. Huber Corporation, but other polishing agents may be employed too, including water-insoluble sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, alumina trihydrate, aluminum silicate, zirconium silicate, calcined alumina, bentonite, silica gel or colloidal silica, and complex amorphous alkali metal aluminosilicates and mixtures thereof. Still other suitable polishing materials include the particulate thermosetting resins described in U.S. Pat. No. 4,070,510, such as melamine-, phenolic-, and urea-formaldehydes, and crosslinked polyepoxides and polyesters.

When visually clear gels are desired, a polishing agent of colloidal silica, such as those which have been sold under the trademark SYLOID® as Syloid 72 and Syloid 74 or under the trademark Santocel® as Santocel 100, and alkali metal aluminosilicate complexes thereof are particularly useful, since they have refractive indices close to the refractive indices of gelling agent-liquid (including water and/or humectant) systems that are often used in dentifrices.

Various other components of toothpastes may be considered to be additional active materials or adjuvants. Included in this group are: other anti-tartar or anti-calculus compounds, such as AHP, PPTA, PBTA and EHDP, zinc compounds, such as zinc chloride, zinc acetate and zinc oxide, and sanguinaria extract; antibacterial agents, such as triclosan; buffers to control pH; bleaching agents and tooth whiteners, such as per-compounds; preservatives; sweeteners, such as potassium (or sodium) saccharin or cyclamate, acesulfam-K, sucralose and aspartame; flavors, such as mint (peppermint and spearmint) and menthol; and dyes and pigments, such as chlorophyll and titanium dioxide. Such water soluble active and adjuvant components of the toothpastes of other oral compositions of this invention, if in soluble salt form, are preferably potassium salts because it appears that potassium cations in such compositions increase desensitization of the tooth nerves by the tooth pain inhibiting potassium salt, such as potassium nitrate and potassium citrate.

Although it is preferred that the oral compositions of this invention be toothpastes or gel dentifrices (including "striped" dentifrices) to be brushed onto the teeth to clean them, and to inhibit tartar development on them, other forms of oral compositions can also be improved by inclusion in the formulas thereof of the anti-tartar and desensitizing ingredients detailed herein. Because the mechanical forces of brushing can be irritating in themselves and can force into the dentin and pulp of sensitive teeth irritating chemicals from foods, tartar deposits, candies, and even from other oral composition components, although the present invention finds greatest use in toothpastes, tooth powders, lozenges and liquid dentifrices can also be significantly improved by inclusion therein of the mentioned anti-tartar and desensitizing components. Other oral preparations that are not intended for brushing into the teeth can also include the anti-tartar and desensitizing components described and among such products are mouth rinses, antiseptic solutions, chewing gums, tooth treating agents, such as plaque locating solutions, and even dental floss and dental tape. In these non-toothpaste or non-dentifrice gel preparations the proportions of anti-tartar pyrophosphate or related compound will be an anti-tartar proportion and that of desensitizing potassium nitrate or potassium citrate will be a desensitizing proportion. The mouth rinses will normally contain water, alcohol, humectant, such as glycerol, sorbitol and/or polyethylene glycol, flavor and sweetener (non-sugar), in addition to the active components mentioned, and the tooth powders will contain mostly a polishing agent, such as Zeodent, Syloid, Santocel or calcium carbonate. The lozenges may include a base of a gummy or polymeric binder, such as carrageenan or alginate (preferably potassium alginate), with a filler, such as calcium carbonate or finely divided silica (micron-sized). Chewing gums may include a natural or synthetic elastomer or rubber base. In the other preparations mentioned the usual product formula may have the described anti-tartar agent and desensitizing agent present too or such may be deposited thereon, as for the dental floss and tape, and preferably water soluble salt components will be potassium salts.

The proportions of anti-tartar and desensitizing components in the invented compositions and articles of this invention have been characterized as anti-tartar and desensitizing proportions thereof, by which it is meant that the proportions of such compounds and mixtures of such compounds in the compositions and products should be sufficient to have the mentioned effects. It is to be understood that for anti-tartar action to be apparent to the user it might take several applications of the anti-tartar preparation to the teeth, and that such application procedure and the type of preparation applied can cause such proportion of the active component to be different, as might the other components of the composition applied. To a lesser extent such could also be true of the desensitizing proportion of the desensitizing agent. However, it has been found that at least 1% of the anti-tartar polyphosphate and at least 2% of the desensitizing potassium nitrate or potassium citrate (or other tooth pain inhibiting potassium compound) are desirably present in all of the oral compositions and articles referred to above, although lower percentages are appropriate for mouth washes. For the toothpastes and dental gels or gel dentifrices the proportion of anti-tartar polyphosphate is normally within the range of 1 to 5%, preferably being in the range of 1.5 to 4% and more preferably being in the range of 2 to 3%, e.g., about 2.5%. That is not to say that as little as 0.5% might not have a positive effect if use is repeated frequently and application thereof to the teeth is careful and diligent. Also, larger proportions than 5%, such as 10%, can be employed, although often such larger "doses" are not needed.

The desensitizing proportion of the tooth pain inhibitor (preferably potassium nitrate or citrate) will usually be in the range of 2 to 10%, preferably being in the range of 3 to 8% and more preferably being in the range of 4 to 6%, e.g., about 5%. Again, as was indicated with respect to the anti-tartar component, lesser proportions may be useful in some circumstances, such as as little as 0.5 or 1% and larger proportions may be employed, but will usually not exceed 15%, and often because of toothpaste taste considerations.

When SAPP (synthetic anionic polymeric polycarboxylate) is present, as is highly desirable, the proportion thereof in the toothpaste will normally be in the range of 0.5 to 4% (although as little as 0.3% may have a useful effect and the upper "limit" can be as high as 10% or more in specific circumstances), preferably 0.8 to 3% and more preferably 1 to 2%, e.g., about 1.5%. When a water soluble fluoride is present in the proportion thereof will usually be that which provides about 100 to 2,300 p.p.m. of fluoride ion ($F^-$) and preferably about 400 to 1,500 p.p.m. of $F^-$ in the composition. For instance, 0.0336% of KF provides 1,099 p.p.m. of $F^-$, 100 p.p.m. of $F^-$ is provided by 306 p.p.m. or 0.0306% of KF, 2,300 p.p.m. of $F^-$ is provided by 7,032 p.p.m. or 0.703% of KF, 400 p.p.m. of $F^-$ is provided by 1,223 p.p.m. or 0.122% of KF and 1,500 p.p.m. of $F^-$ is provided by 4,586 p.p.m. or 0.459% of KF. Higher proportions, even up to 10,000 p.p.m. of $F^-$, may be used for professional fluoride treatments for anti-caries activity. From the above ranges it is seen that the percentages of KF to provide the desired fluoride ion will usually be in the range of 0.03 to 0.7% preferably 0.1 to 0.5% and more preferably 0.3 to 0.4%, e.g., about 0.3 or 0.34%, for the toothpaste and gels (but variable for other compositions). The toothpaste will usually include in the base portion thereof 0.5 to 5% of surfactant, which will preferably be a synthetic organic anionic dental detergent, preferably 0.8 to 3% thereof and more preferably 0.8 to 2.5% thereof and most preferably 1.2 to 2%, e.g., about 1.2%. The content of polishing agent will normally be in the range of 10 to 50%, preferably 15 to 35% and more preferably 15 to 30%, e.g., about 23% of polishing agent (preferably silica or siliceous polishing agent and more preferably precipitated amorphous hydrated silica). The humectant content will usually be in the range of 10 to 50%, preferably 15 to 40%, and the humectant will preferably be glycerol, sorbitol or polyethylene glycol or a mixture of any two or more thereof. More preferably the humectant will be a mixture of two or more of such materials, with the polyethylene glycol being of a molecular weight in the range of 200 to 1,000. Most preferably the humectant will comprise 5 to 20% of glycerol, 5 to 25% of sorbitol and 1 to 10% of polyethylene glycol of a M.W. of 400 to 800, e.g., about 10% of glycerol, about 16% of sorbitol and about 3% of polyethylene glycol of a M.W. of about 600. The thickener or gelling agent component of the toothpastes will normally be in the range of 0.2 to 5%, preferably 0.3 to 3% and more preferably 0.5 to 2%, with preferred such gelling agent components being carrageenan, carboxymethylcellulose, xanthan gum or a mixture thereof, e.g., 0.8 or 1.2% of carrageenan, carboxymethylcellulose or xanthan, or a mixture of about equal parts of each. The water in the toothpaste, which forms part of the vehicle, with the humectant, normally comprises 20 to 50% of the toothpaste, preferably 25 to 45%, and more preferably 30 to 40%, e.g., about 35%.

Other components, which may be considered to be parts of the adjuvants in the invented toothpastes, include pigment, sweetener and flavor. In the preferred white dental cream formulations the pigment will be titanium dioxide, rutile, and the proportion thereof will normally be in the range of 0.2 to 1%, preferably 0.4 to 0.8% and more preferably 0.4 to 0.6%, e.g., about 0.5%. The sweetener content will normally be that of an artificial or synthetic sweetener (non-sugar) and the normal proportion thereof present will be in the range of 0.2 to 0.8%, preferably 0.3 to 0.7% and more preferably 0.4 to 0.6%, e.g., about 0.5%, although for cyclamate salt sweeteners such range is typically 3 to 7%. The flavor content, which is preferably of a mixed peppermint/menthol flavor, will usually be in the range of 0.5 to 2%, preferably 0.7 to 1.5% and more preferably 0.8 to 1.2%, e.g., about 1%. F.D & C. Grade dyes may be used in appropriate amounts to provide desired colors. The contents of other components or adjuvants of the toothpaste formula will normally not exceed 10%, often will be less than 5%, and can be as low as 0%, for instance 0.5 to 5% of anionic surfactant, such as 0.8 to 3% of alkali metal sulfate, for instance 0.8 to 1.5%, say 1.2% of potassium lauryl sulfate.

To make the invented toothpastes a particular process is preferred because it results in excellent toothpastes which are of the desired pH and viscosity, and in which the active components are of improved stabilities. In such process the glycerol and polyethylene glycol components of the humectant are mixed together first in a conventional mixer and then the thickener, copolymer, alkali metal fluoride and potassium pyrophosphate are dispersed in the humectant mix, with mixing, and such mixing is continued until the mixture becomes a slurry, which is smooth in appearance, after which the sorbitol is admixed with the smooth slurry and water is added and the desensitizing agent(s) is/are admixed with the thinned slurry. All such mixings are at room temperature, in the range of 20° to 30° C. Next, the gel phase produced may be heated to a temperature in the range of 55° to 75° C., with mixing, and mixing is continued for 10 to 30 minutes after the elevated temperature in the given range has been reached. The copolymer if initially in acidic form, is the neutralized with alkali metal hydroxide, preferably potassium hydroxide, to a pH in the range of 6 to 8, preferably 7, with mixing, and such mixing is continued for another 10 to 30 minutes after completion of the addition of the alkali metal hydroxide. Then the gel phase resulting, if heated, is cooled to a temperature of the range of 35° to 45° C., after which the siliceous polishing agent is admixed with the gel phase and mixing is continued for an additional 10 to 30 minutes under a vacuum in the range of 5 to 100 millimeters of mercury, preferably 5 to 50 mm. Hg, resulting in production of a paste of gel. The last step of the process (excluding additions of pigment, flavor, sweetener and other adjuvants) is the admixing of surfactant, preferably anionic detergent, with the paste or gel, which is followed by mixing for another 3 to 10 minutes under a vacuum of 5 to 50 mm. Hg. The product resulting is a stable anti-tartar desensitizing toothpaste which is of a viscosity like that of normal toothpastes, about 100,000 to 500,000 centipoises, of a pH in the range of 6 to 8, preferably 6.5 to 7.5, e.g., 7, of satisfactor flavor, (especially when a mint/menthol flavor is present), and not excessively salty. In the above description of the manufacturing method a humectant mixture was employed and no flavor, sweetener and pigment additions were mentioned. If one or more of the described humectants or of any other optional component(s) of the formula is/are not present in the formula the addition steps mentioned above that apply to such components may be omitted. Also, the sweetener and pigment may be added with the thickener, copolymer, fluoride and polyphosphate to the glycerol/polyethylene glycol mixture and the flavor may be added with the surfactant near the end of the procedure.

The invented toothpastes may be made by other methods than that described above but it has been found that the described procedure results in better toothpastes, and therefore it is preferred. As to other embodiments of the invention, gel dentifrices may be made in substantially the same manner, with normal adjustments of the formula components and proportions known to those of skill in the toothpaste formulation art. To make tooth powders it is only a matter of blending in the various active components with a polishing agent, and to make mouth washes or other liquid preparations the main active components may be dissolved or dispersed in an appropriate liquid medium, usually an aqueous alcoholic medium, and polymeric, gummy and insoluble materials will normally be omitted, although the SAPP may be present. Other types of oral compositions and preparations may be prepared by appropriate conventional procedures, with appropriate additions of the usual active components and of the appropriate usual supplements and adjuvants during the manufacturing process.

The following examples are given to illustrate the invention and are not to be considered as limiting the scopes of the claims. Unless otherwise indicated all parts and percentages are by weight and all temperatures are in °C.

| Component | Percent (by weight) |
| --- | --- |
| Glycerol (99.3% pure) | 10.00 |
| Polyethylene glycol 600 | 3.00 |
| *Carrageenan (90% active) | 0.85 |
| Sodium saccharin | 0.40 |
| Sodium fluoride | 0.243 |
| Titanium dioxide, F.D. & C. grade | 0.50 |
| Tetrapotassium pyrophosphate | 2.50 |
| Potassium nitrate | 5.00 |
| **SAPP (copolymer of maleic anhydride with vinyl methyl ether, of an average M.W. of about 70,000 by vapor pressure osmometry) | 11.54 |
| ***Water | 17.817 |
| Sorbitol solution (70% aqueous solution) | 22.50 |
| Potassium hydroxide | 0.50 |
| ****Silica (precipitated amorphous hydrated silicon dioxide) | 23.0 |
| Sodium lauryl sulfate | 1.20 |
| +Peppermint flavor | 0.95 |
| | 100.00 |

*Viscarin ® TP-206, manufactured by Marine Colloids Division of FMC Corporation
**Gantrez ® S-97, liquid, manufactured by GAF Corporation
***Deionized and irradiated (ultraviolet ray treatment)
****Zeodent ® 115, manufactured by J.M. Huber Corporation
+Includes menthol A toothpaste of the above formula is made by the procedure previously described somewhat generally in this specification. First, the Viscarin, Gantrez, sodium saccharin, sodium fluoride, tetrapotassium pyrophosphate and titanium dioxide are dissolved and/or dispersed in a solution of the polyethylene glycol 600 in glycerol at room temperature and after the admixing is completed mixing is continued until the appearance of the mixture is smooth, which takes about five minutes. The sorbitol is then admixed with the smooth slurry and the deionized water is admixed with the resulting slurry, after which the potassium nitrate is admixed, which takes only about 3 to 5 minutes. The gel phase intermediate product obtained is then heated to about 65° C. and mixing is continued for 18 minutes after that temperature is reached. Potassium hydroxide is then admixed with the heated gel phase intermediate, which takes about two minutes, and then, after 20 minutes further mixing the mix is cooled to about 38° C. The cooled gel phase is then added to a Ross pot and the Zeodent is admixed with it in the pot under full vacuum (about 30 mm. of Hg) for ten minutes, after which the walls of the pot are scraped down and mixing is resumed for an additional ten minutes under the same full vacuum. Finally the sodium lauryl sulfate and flavor are admixed and mixing is continued for about five minutes under such full vacuum. The toothpaste resulting is of a pH of 7 and a viscosity in the desirable range for toothpaste, of a viscosity of about 400,000 centipoises or a Brookfield consistency of about 20–40, and such consistency is substantially constant on storage for over 100 days, after an initial increase. To increase the thickness of the toothpaste one may increase the carrageenan content to 1.2 or 1.5%, if desired, with a corresponding decrease in the water content.

The toothpaste made is effective for tartar control, with simulated tartar being reduced by it, and tooth pain and sensitivity during brushing are also reduced. In vitro tests show that the toothpaste, when applied to tooth specimens, decreases the sizes of tubules of the dentin, which effect appears to be due, at least in part, to the presence of the SAPP in the formula, but the potassium and nitrate ions can still pass through such tubules to reach the pulp, where they can act to decrease sensitivity of the nerves to pain inducing stimuli, such as sugars. Further tests indicate that the toothpaste made reduces tooth pain and sensitivity, compared to a control, and it is considered that the product of this example, containing additional potassium ion, over that of the potassium nitrate alone, is even more effective than a similar potassium nitrate (only) toothpaste in desensitizing the teeth to pain.

A further advantage of the invented composition of this example is in the neutralization of the SAPP or equivalent polymer with a potassium-containing neutralizing agent, such as potassium hydroxide. The making of the potassium SAPP initially avoids removal of potassium ion from the toothpaste (from the potassium nitrate component thereof) by the SAPP during storage before use, and during use, which removal could cause a decrease in the desensitizing action attributable to the potassium ion. The employment of potassium pyrophosphate also adds potassium ion to the system, for pain diminution, while still allowing the pyrophosphate to fight tartar. In further improvements of the formula and similar formulas sodium fluoride, sodium saccharin sodium lauryl sulfate and any other suitable sodium or other metal salts and compounds have the cations thereof replaced by potassium so as further to improve the desensitizing effect of the toothpaste.

In variations of the formula the polyethylene glycol is omitted from the formula, being replaced by glycerol, the Viscarin TP-206 is replaced by Viscarin TP-305B, the sodium saccharin is replaced by aspartame, the potassium nitrate is replaced by potassium citrate or by a 1:1 mixture of the nitrate and citrate, the Gantrez is replaced by other Gantrezes, including Gantrezes AN-119, AN-139 and AN-169, and by a 1:1 mixture of Gantrez S-97 with each of such other Gantrezes, and the Zeodent 115 is replaced by Zeodent 113. Also, as described in U.S. patent application Ser. No. 07/631,232 an anti-calculus compound, such as AHP, can be included in the toothpaste and other oral compositions. Instead of AHP and other AAP's mentioned in that application, there may be employed PPTA, PBTA and EHDP, as the acids or alkali metal salts, preferably as the potassium salts. These anti-calculus agents may be 0.2 to 2 or even 5%, preferably 0.5 to 1.5%, and may supplement the polyphosphate and in some cases can replace it in whole or in part, preferably when there is provided in the formula enough potassium to increase the desensitizing action of the potassium salt tooth pain inhibitor. Additionally, the flavor may be changed as desired, so as better to overcome any perceived saltiness by some users who are more sensitive to the presence of salty materials than are most persons. However, it is considered that the present compositions are surprisingly good tasting, considering the relatively high proportion of salts in them.

In other variations of the invention dyes may be incorporated in this formula to produce colored dentifrices, and such may be dispensed from the same collapsible tubes or from other dispensers to produce striped toothpastes of contrasting colors (such as red/white). Alternatively, by omission of the pigment and by use of a suitable polishing agent of an index of refraction like that of the vehicle or base of the formula one may make a transparent, translucent or cloudy toothpaste or gel dentifrice. All such products will have both anti-tartar and desensitizing properties.

EXAMPLE 2

A toothpaste of the formula given in Example 1 is made, but the carrageenan is replaced with sodium carboxymethylcellulose (CMC 12M31P, from Hercules Corporation). The toothpaste made is satisfactorily anti-tartar and desensitizing but may be considered to be of a lower viscosity than desired, so the proportion of such CMC is increased to 1.5% with the water being reduced to 17.07% to compensate, and a toothpaste of greater viscosity or body is obtained. Such toothpaste can be further improved by replacement of all sodium compounds therein with corresponding potassium compounds, e.g., by employing 0.336% of KF, and adjusting water contents accordingly.

Instead of utilizing only CMC as the gelling agent in this formula there may be employed a mixture of CMC and carrageenan, such as a 1:1 mixture, with the total proportion being about 1.5%. Also, although it is preferred to employ siliceous polishing agent, such may be replaced with other acceptable polishing agents, such as dicalcium phosphate, calcium carbonate and resinous polishing agents, that are compatible with the gelling agent and the other toothpaste components. Also, it is desirable for all the sodium compounds of the formula and its variations to be replaced by corresponding potassium compounds. All such variations in the composition will result in toothpastes that are effectively anti-tartar and are useful in the brushing of sensitive teeth. The toothpastes of this and the other examples herein perform several interrelated functions, cleaning the teeth while desensitizing them to the cleaning operation, which could otherwise cause some irritation and pain, removing tartar, and calculus, which could harbor sugars and other compounds that could cause pain to sensitive teeth, hardening the teeth and helping to close off tubules or channels through which irritating chemicals could be transported to the dentin and pulp to cause pain in sensitive teeth, closing off such tubules to sugar migration with a SAPP that does not prevent desensitizing ions from reaching tooth interiors to reduce pain of sensitive teeth, and improving desensitizing action of potassium nitrate with other potassium salt components of the toothpaste. The results of all such actions are toothpastes that are effective anti-tartar and desensitizing oral compositions.

EXAMPLE 3

A modification of the toothpaste formula of Example 1 is made in which the carrageenan gelling agent is desirably replaced by xanthan gum, and the resulting toothpaste, produced by the same method as described in Example 1, is found to be a satisfactory anti-tartar and desensitizing one. It is also found to be of an acceptable viscosity or thickness, being measurably thicker than the toothpaste of Example 1. As with the other toothpastes of Examples 1 and 2, the toothpaste is not excessively salty in taste and any saltiness is hardly discernible in the presence of the peppermint/menthol flavoring agent.

In variations of the formula other bases may be employed, containing different polishing agents, humectants, gelling agents surfactants, fluorides, SAPP's, flavors, sweeteners, pigments, polyphosphates and desensitizing potassium salts, and equivalent anti-tartar and desensitizing toothpastes will result. Specifically, the gelling agent employed may be a mixture of one part of carrageenan and one part of xanthan gum or may include a Laponite®, the surfactant may be sodium or potassium cocomonoglyceride sulfate or sodium or potassium sarcosine, the polishing agent may be other silicas, such as Syloids® or Santocels®, or calcium carbonate or calcium phosphates, the SAPP may be a Carbopol®, the fluoride may be potassium monofluorophosphate, the pigment may be omitted and the potassium nitrate may be replaced by potassium citrate or potassium oxalate, and useful anti-tartar and desensitizing toothpastes or gels will result. Also, as described in Example 2, AHP, AAP's, PPTA, PBTA and EHDP may be present in the disclosed effective proportions with the polyphosphate or in partial or complete replacement of it and such applies to Example 1 and to Example 4, too.

Other oral compositions than toothpastes and gel dentifrices may also be made by employing the required components of the invention in a liquid medium, to make a mouthwash. In one such product the mouthwash base or solvent system will be 20% of ethanol in water, and will contain about ⅒ of each of the percentages of potassium pyrophosphate and potassium nitrate in the toothpaste of Example 1. In another product the mouthwash will also contain about 0.05% or 0.08% of sodium or potassium fluoride. A chewing gum may contain the same proportions of potassium pyrophosphate, potassium nitrate and sodium or potassium fluoride and SAPP as in Example 1, in a chicle or rubber base. A tooth powder may contain the same proportions of such four components, together with flavoring, in a base of Zeodent or other polishing agent. Such powder may be compressed to tablet, lozenge or pastille form, for crushing before use as a tooth powder, and a binding agent, such as starch or more gelling agent, may be used to aid in binding the components together. Additionally, other oral compositions and articles may be made, using the various components of the toothpastes of Examples 1–3 or some of them (but including the potassium salt pain killer and the polyphosphate or anti-calculus compound). All the products so described will have anti-tartar and desensitizing properties, and in all of them it will be desirable to utilize potassium compounds to the extent possible.

In all the invented oral compositions, including the toothpastes and gel dentifrices, the potassium polyphosphate or other anti-calculus agent and the desensitizing agent cooperate to produce improved desensitizing action, and such improvement is further promoted by the presence of the other described components of such dentifrices, including the SAPP, fluoride, surfactant, and other components of such compositions, especially when such are in the forms of potassium compounds, such as potassium salts.

Although the invention has been described with respect to highly preferred embodiments thereof it really has broader application in the area of dentifrices and tooth treatments. As was previously indicated, other anti-tartar and anti-calculus compounds and mixtures of such compounds, such as various AAP's (azacycloalkane-2,2-diphosphonic compounds, as described in Ser. No. 07/631,232), including AHP, may be employed instead of alkali metal polyphosphate, preferably as the potassium salt. Anti-calculus phosphono compounds that are useful include PPTA, PBTA and EHDP, and AHP is a preferred AAP. The proportion of such anti-calculus compound will usually be in the range of 0.2 to 5%, such as 0.5 to 1.5%, and it will preferably be present as a potassium salt. The tooth pain inhibitor will usually be 2 to 10% of the composition, preferably 3 to 8% and the inhibitor will preferably be potassium nitrate or potassium citrate. When potassium pyrophosphate is not employed as the anti-tartar agent, so its potassium content is not present to help increase the pain inhibiting properties of the pain inhibitor other sources of potassium should be present, such as potassium fluoride, potassium saccharin, potassium detergent, etc., and the potassium content of the composition, in addition to the potassium of the pain inhibitor, should be in the range of 0.2 to 5%, preferably 0.5 to 3%, and such potassium should be in ionizable form. In such concentrations the potassium will improve desensitizing action of the tooth pain inhibitor and will not make the toothpaste or oral composition excessively salty. Of course, for other compositions which are normally more dilute (mouth washes, for example) or more concentrated, proportions of potassium may be adjusted accordingly.

The invention has been described in conjunction with illustrative embodiments thereof but is not to be considered to be limited to these because one of skill in the art will be able to utilize substitutes and equivalents thereof without departing from the bounds of the invention and the spirit thereof.

What is claimed is:

1. A desensitizing, anti-tartar toothpaste which consists essentially of an orally acceptable vehicle or base for such composition, an effective anti-tartar proportion anti-tartar agent of (a) tetrasodium pyrophosphate, (b) disodium pyrophosphate, (c) mixtures of (a) and (b) or (d) mixtures of at least one of (a) and (b) with a potassium pyrophosphate and a desensitizing proportion of a tooth pain inhibiting potassium salt which passes through exposed dentin tubules to tooth nerves or neurons, which tooth pain inhibiting potassium salt is potassium nitrate, potassium citrate, potassium oxalate or a mixture of two or more thereof;

wherein there is present in said toothpaste from said anti-tartar agent or from an additional material a source of potassium ions in addition to the tooth pain inhibiting potassium salt, the oral composition having a potassium content, in addition to the potassium pain inhibitor, in the range 0.2 to 5% by weight such potassium being in ionizable form.

2. A toothpaste according to claim 1 which comprises 0.5 to 5% of anionic surfactant, 10 to 50% of polishing agent, 10 to 50% of humectant, 0.2 to 5% of thickener, 1 to 5% of said pyrophosphate, 2 to 10% of said potassium nitrate, potassium citrate or a mixture thereof and 20 to 50% of water.

3. A toothpaste according to claim 2 wherein the anionic surfactant is an anionic detergent, the polishing agent is a siliceous polishing agent, the humectant is selected from the group consisting of glycerol, sorbitol and polyethylene glycol, and mixtures of two or more thereof, the thickener is selected from the group consisting of natural and synthetic gums and colloids and the desensitizing compound is potassium nitrate, potassium citrate or a mixture thereof.

4. A toothpaste according to claim 3 which comprises 0.8 to 3% of alkali metal lauryl sulfate, 15 to 35% of silica, 15 to 40% of a mixture of two or more of glycerol, sorbitol and polyethylene glycol of molecular weight in the range of 200 to 1,000, 0.3 to 3% carrageenan, carboxymethylcellulose, xanthan or a mixture thereof, 1.5 to 4% of pyrophosphate, 3 to 8% of potassium nitrate and 25 to 45% of water.

5. A toothpaste according to claim 3 which comprises 0.8 to 3% of alkali metal lauryl sulfate, 15 to 35% of silica, 15 to 40% of a mixture of two or more of glycerol, sorbitol and polyethylene glycol of molecular weight in the range of 200 to 1,000, 0.3 to 3% of carrageenan, carboxymethylcellulose, xanthan or a mixture thereof, 1.5 to 4% of said pyrophosphate, 3 to 8% of potassium citrate and 25 to 45% of water.

6. A toothpaste according to claim 4 which comprises 0.8 to 1.5% of potassium lauryl sulfate, 15 to 30% of amorphous hydrated silica, 5 to 20% of glycerol, 5 to 25% of sorbitol, 1 to 10% of polyethylene glycol of molecular weight in the range of 400 to 800, 0.5 to 2% of carrageenan, 2 to 3% of said pyrophosphate, 4 to 6% of potassium nitrate and 30 to 40% of water.

7. A toothpaste according to claim 5 which comprises 0.8 to 1.5% of potassium lauryl sulfate, 15 to 30% of amorphous hydrated silica, 5 to 20% of glycerol, 5 to 25% of sorbitol, 1 to 10% of polyethylene glycol of molecular weight in the range of 400 to 800, 0.5 to 2% of carrageenan, 2 to 3% of said pyrophosphate, 4 to 6% of potassium citrate and 30 to 40% of water.

8. A toothpaste according to claim 6 which comprises about 1.2% of potassium lauryl sulfate, about 23% of precipitated amorphous hydrated silica, about 10% of glycerol, about 16% of sorbitol, about 3% of polyethylene glycol of molecular weight of about 600, and 0.8% of carrageenan, about 2.5% of said pyrophosphate, about 5% of potassium nitrate and about 30 to 35% of water.

9. A toothpaste according to claim 7 which comprises about 1.2% of potassium lauryl sulfate, about 23% of precipitated amorphous hydrated silica, about 10% of glycerol, about 16% of sorbitol, about 3% of polyethylene glycol of molecular weight of about 600, and 0.9% of carrageenan, about 2.5% of said pyrophosphate, about 5% of potassium citrate and about 30 to 35% of water.

10. A toothpaste according to claim 1 in which said polyphosphate is tetrasodium pyrophosphate.

11. A process for the preparation of a desensitizing anti-tartar toothpaste according to claim 3 which comprises mixing together glycerol and polyethylene glycol components of the humectant component of such a toothpaste formula, dispersing in such mixture the thickener, copolymer and sodium pyrophosphate, with mixing, until the mixture becomes a slurry, adding water to the resulting slurry, admixing with the thinned slurry potassium nitrate and/or potassium citrate, to produce a gel phase, neutralizing the copolymer in the gel phase with alkali metal hydroxide, to a pH in the range of 6 to 8, with mixing, and continuing such mixing for 10 to 30 minutes after completion of addition of the alkali metal hydroxide, admixing the siliceous polishing agent with the gel phase, mixing for 10 to 30 minutes under a vacuum in the range of 5 to 50 millimeters of mercury, to produce a paste or gel and mixing for 3 to 10 minutes under a vacuum in the range of 5 to 50 mm. of mercury; the toothpaste having a potassium content, in addition to the potassium pain inhibitor, in the range 0.2 to 5%, such potassium being in ionizable form.

12. A process according to claim 11 wherein said gel phase resulting from admixing of the potassium nitrate and/or potassium with the thinned slurry is heated to a temperature in the range of 55° to 70° C., with mixing, and mixing is continued for 15 to 30 minutes after such temperature is reached, and after completion of addition of the potassium hydroxide said gel phase is cooled to a temperature in the range of 35° to 45° C.

13. A process for desensitizing sensitive teeth and reducing tartar and inhibiting tartar formation which comprises applying to said teeth a composition according to claim 1.

14. An oral composition according to claim 1 wherein said pyrophosphate is tetrasodium pyrophosphate.

15. A process according to claim 11 wherein said alkali metal hydroxide is potassium hydroxide.

* * * * *

UNITED STATES PATENT AND TRADEMARK OFFICE
CERTIFICATE OF CORRECTION

PATENT NO. : 5,505,933
DATED : April 9, 1996
INVENTOR(S) James Norfleet, et al

It is certified that error appears in the above-indentified patent and that said Letters Patent is hereby corrected as shown below:

Cover page, left column, under "Related U.S. Application Data" after "Division of Ser. No. 265,883, June 27, 1994" insert:

--, Pat. No. 5,503,823, which is a continuation of Serial No. 71,384, June 4, 1993, Pat. No. 5,352,439, which is a continuation of Ser. No. 778,532, Oct. 17, 1991, Pat. No. 5,240,697--.

Column 1, line 5, after "on June 27, 1994" insert

--which is a continuation of application S.N. 08/071,384, filed June 4, 1993, now U.S. Patent 5,352,439, issued October 4, 1994, which is a continuation of S.N. 07/778,532, filed October 17, 1991, now U.S. Patent 5,240,697, issued August 31, 1993--.

Signed and Sealed this

Twenty-fifth Day of February, 1997

Attest:

BRUCE LEHMAN

*Attesting Officer*          *Commissioner of Patents and Trademarks*